United States Patent [19]

Farina et al.

[11] Patent Number: 5,252,744
[45] Date of Patent: Oct. 12, 1993

[54] PROCESS FOR PREPARING METHYLOLHYDANTOINS

[75] Inventors: Thomas E. Farina, Flemington, N.J.; Douglas A. Burg, Easton, Pa.

[73] Assignee: Lonza Inc., Annandale, N.J.

[21] Appl. No.: 887,356

[22] Filed: May 21, 1992

[51] Int. Cl.$^5$ .................. C07D 233/74; C07D 233/78
[52] U.S. Cl. .................. 548/317.1; 548/319.1
[58] Field of Search ............. 548/308, 312, 319.1, 548/317.1; 514/389

[56] References Cited

U.S. PATENT DOCUMENTS

| | | | |
|---|---|---|---|
| 3,987,184 | 10/1976 | Foelsch et al. | 548/312 |
| 4,908,456 | 3/1990 | Farina et al. | 548/312 |
| 5,036,095 | 7/1991 | Andermann | 514/389 |

Primary Examiner—Joseph Paul Brust
Assistant Examiner—MarySusan H. Gabilan
Attorney, Agent, or Firm—Darby & Darby

[57] ABSTRACT

There are provided methods for producing solid anhydrous methylolhydantoins. Initially, an aqueous stirrable medium is dehydrated and heated to yield a substantially anhydrous stirrable melt. The aqueous stirrable medium includes (A) a solute selected from the group consisting of (i) a dimethyloldimethylhydantoin, (ii) a hydantoin reactant, (iii) a formaldehyde source reactant, or (iv) a combination of any of the foregoing; and (B) optionally a catalyst. A molten system is then provided by adding, to the stirrable melt, a reactant mixture which includes (A)(i) the same or a different hydantoin reactant, (ii) a substantially anhydrous formaldehyde source reactant which may be the same as or different than the formaldehyde source reactant, or (iii) a combination thereof; and (B) optionally, the same or a different catalyst; wherein the molten system includes (i) at least one hydantoin reactant and (ii) at least one dehydrated formaldehyde source reactant or substantially anhydrous formaldehyde source reactant.

23 Claims, No Drawings

PROCESS FOR PREPARING METHYLOLHYDANTOINS

FIELD OF THE INVENTION

This invention relates to the preparation of solid anhydrous methylolhydantoins. The methods of the present invention eliminate processing constraints typically associated with solids blending and permit the use of classical liquid handling reactors for the production of solid, anhydrous hydantoins.

BACKGROUND OF THE INVENTION

Methylolhydantoins are colorless, odorless, water soluble compounds that are useful as formaldehyde donors in certain preparations that are susceptible to microbial growth. These preparations may include industrial products such as liquid detergents, water-based surfactants, soft soaps, water-based paints, fabric softeners, room deodorizers/air fresheners, polymer emulsions, protective coatings for textiles, architectural coatings, water-based gels, sealants and caulks, latexes for paper coatings, water-based inks, wood preservatives, and the like. They may also include personal care products such as cosmetics, shampoos, creams, lotions, powder products, and the like.

Methylolhydantoins, such as monomethyloldimethylhydantoins (MDMH) or dimethyloldimethylhydantoins (DMDMH) are typically produced as aqueous solutions, usually by methylolating one mole of DMH with one or two moles respectively of formaldehyde. Particularly, Foelsch, in U.S. Pat. No. 3,987,184, discloses a method for the production of aqueous solutions of DMDMH wherein 1.85 to 2.4 moles of formaldehyde (aqueous) per mole of 5,5-dimethylhydantoin (5,5-DMH) are reacted at a pH of from about 7 to about 9, for a period of about 20 minutes, at a temperature of from about 22° C. to 65° C.

Aqueous solutions of MDMH and DMDMH increase the cost of the product due to the expenses of the solvent and of transporting the volume of the aqueous solutions, however. Therefore, a dry product is desirable. The most simple method of producing a dry product is a separation process which separates the methylolhydantoin from the solvent. However, separation processes typically are tedious and time-consuming and involve one or more processing steps.

Farina et al., U.S. Pat. No. 4,908,456, disclose the production of dry, crystallized methylolhydantoins by mixing hydantoin, a formaldehyde source such as paraformaldehyde, and a catalyst, and then reacting the components at elevated temperatures. However, because the reactants are dry blended and are then heated to extreme temperatures, the equipment required is complicated and is not easily accessible.

SUMMARY OF THE INVENTION

Liquid-based methods for the production of solid, anhydrous methylolhydantoins have been discovered. These methods can be practiced in typical liquid handling reactors because the initially charged reactor contains an aqueous medium. The reactor does not, at any point of the present process, contain completely solid intermediate materials. Therefore, the need for specialized dry processing equipment that can also be subjected to the heat of the reactions herein is avoided.

According to a first embodiment of the present invention (the aqueous medium/molten system method), there is provided a method for producing solid anhydrous methylolhydantoin comprising:

(a) dehydrating and heating an aqueous stirrable medium to yield a substantially anhydrous stirrable melt, said aqueous stirrable medium comprising:
  (A) a solute selected from the group consisting of
    (i) a dimethyloldimethylhydantoin,
    (ii) a hydantoin reactant,
    (iii) a formaldehyde source reactant, or
    (iv) a combination of any of the foregoing; and
  (B) optionally a catalyst;

(b) providing a molten system by adding to said stirrable melt, a reactant mixture comprising:
  (A)(i) the same or a different hydantoin reactant,
    (ii) a substantially anhydrous formaldehyde source reactant which may be the same as or different than the formaldehyde source reactant, or
    (iii) a combination thereof; and
  (B) optionally, the same or a different catalyst;
wherein the molten system includes (i) at least one hydantoin reactant and (ii) at least one dehydrated formaldehyde source reactant or substantially anhydrous formaldehyde source reactant;

(c) reacting (i) the at least one hydantoin reactant and (ii) the at least one dehydrated formaldehyde source reactant or substantially anhydrous formaldehyde source reactant in the molten system, while removing reaction water, to yield anhydrous molten methylolhydantoin; and (d) solidifying the molten methylolhydantoin.

In a second contemplated embodiment (the consolidated system method), solid anhydrous methylolhydantoin is produced by reacting, in an aqueous stirrable medium as above, a reactant mixture of (i) the same or a different hydantoin reactant, (ii) a substantially anhydrous formaldehyde source reactant which may be the same as or different than the formaldehyde source reactant, or (ii) a combination thereof and (iv) optionally, the same as or different catalyst; wherein (i) at least one hydantoin reactant and (ii) at least one formaldehyde source reactant or substantially anhydrous formaldehyde reactant is present; while heating to at least the melting temperature of the methylolhydantoin and while removing substantially all water; to yield a molten methylolhydantoin; and subsequently solidifying the molten methylolhydantoin.

These methods can be practiced as batch processes or as semi-continuous processes.

DETAILED DESCRIPTION OF THE INVENTION

DMDMH is a formaldehyde donor which is the diformylated product of DMH and formaldehyde. MDMH is first formed as an intermediate. MDMH, itself, is a formaldehyde scavenger containing about 19% by weight of bound, but available, formaldehyde. Subsequent reaction of MDMH with formaldehyde yields DMDMH which theoretically contains 31.9% of bound but available, formaldehyde.

Initially in the methods of the present invention, an aqueous, stirrable reaction medium is provided. Because the initial reaction medium is liquid-based, typical liquid handling reactors, i.e. stirred tank-type, Pfaudler and the like, may be used. Special reactors adapted for simultaneously blending and heating dry reactants or blends are not required.

The aqueous stirrable reaction medium can be a solution, a mixture, particularly a slurry, or combinations thereof comprised of a methylolhydantoin or a methylolhydantoin precursor, termed herein a "solute", suspended, dissolved, or carried in an aqueous vehicle or solvent. Suitable solutes for the medium are DMDMH; hydantoin reactants, including but not limited to DMH and/or MDMH; formaldehyde source reactants; or any combination thereof. Optionally, a catalyst, as described below, may be added.

Suitable DMDMH solutes include, but are not limited to, DMDMH such as 1,3-dimethylol-5,5-dimethylhydantoin, MDMH such as 1-or 3-methylol-5,5-dimethylhydantoin. Suitable DMH's for use as hydantoin reactant solutes in the aqueous stirrable medium include, but are not limited to, dimethylhydantoins such as 5,5-dimethylhydantoin, monomethylol-5,5-dimethylhydantoin, 5-ethyl-5-methylhydantoin, or any combination thereof. Suitable MDMH hydantoin reactant solutes include, but are not limited to, 1-or 3-methylol-5-ethyl-5-methylhydantoin, or a combination thereof.

Suitable formaldehyde source reactants for use as solutes in the aqueous stirrable medium include any formaldehyde that is water-soluble, and preferably para-formaldehyde, formalin or the like. Para-formaldehyde is a formaldehyde polymer having the chemical formula $HO(CH_2O)_n-H$ where n is about 8-100.

Hydantoin reactants suitable for addition to the stirrable melt or reaction in the stirrable medium include any hydantoin reactants known in the art which react with substantially anhydrous formaldehyde in the presence or in the absence of a catalyst and in a near water-free system, particularly as in the molten system of the present invention. Combinations of more than one hydantoin reactant may be used. These hydantoin reactants include, but are not limited to, DMH such as 5,5-dimethylhydantoin, MDMH such as 1-monomethylol-5,5-dimethylhydantoin, and 5-ethyl-5-methylhydantoin or mixtures thereof.

The substantially anhydrous formaldehyde source reactant typically has a water content of no more than one percent by weight. Preferably, the substantially anhydrous formaldehyde source reactant is para-formaldehyde.

Typical catalysts for use in the stirrable medium or for addition with the hydantoin and/or formaldehyde reactants include, but are not limited to, alkali metal and alkaline earth metal salts such as sodium carbonate, sodium bicarbonate, and sodium hydroxide.

The hydantoin reactant or formaldehyde source reactant that react ultimately to yield the solid, anhydrous methylolhydantoin, may be initially supplied from either the aqueous stirrable medium or from the reactant mixture, provided that at least one hydantoin reactant and at least one formaldehyde source reactant is present for the reaction.

Preferably, the mole ratio of hydantoin reactant to dehydrated formaldehyde source reactant or substantially anhydrous formaldehyde source reactant, reacted in the molten system ranges from about 1:1 to about 1:2. The mole ratio of aqueous stirrable medium or stirrable melt to hydantoin reactant is a function of reactor design and can vary widely as long as there is enough material present to be stirrable in the reactor by, for example, an agitator. Such designs would be known to one of ordinary skill in the art. Preferably, this mole ratio ranges from about 1 to about 0.1.

The composition of the methylolhydantoin produced by the present invention is dependent upon the methylolhydantoin or hydantoin incorporated in the stirrable medium and/or the hydantoin reactant incorporated in the molten system, as well as upon the mole ratio of the reactants. For example, when DMH, and preferably 5,5-dimethylhydantoin, is in the medium or is the hydantoin reactant, solid anhydrous MDMH, and preferably 1- or 3-methylolhydantoin, is produced if the DMH:formaldehyde source reactant mole ratio is about 1:1. When the mole ratio is between about 1:1 and above 1:2, a mixture of MDMH, as above, and DMDMH, preferably 1,3-dimethylol 5,5-dimethylhydantoin, is produced. As the mole ratio reaches 1:2, the product is nearly entirely DMDMH. If the methylolhydantoin in the medium or the hydantoin reactant is MDMH, and preferably monomethylol-5,5-dimethylhydantoin, the product typically is DMDMH, and preferably 1,3-dimethylol-5,5-dimethylhydantoin. When the methylolhydantoin in the medium or the hydantoin reactant is ethylmethylhydantoin (EMH), and preferably 5-ethyl-5-methylhydantoin, the product will be monomethylolethylmethylhydantoin (MEMH), preferably 1- or 3-methylol-5-ethyl if the EMH:formaldehyde source reactant mole ratio is about 1:1. If the mole ratio is between about 1:1 and 1:2, a mo-mixture of MEMH and dimethylolethylmethylhydantoin (DMEMH) is produced. As the mole ratio reaches 1:2, the product is nearly entirely DMEMH. Mixtures of methylolhydantoins or hydantoins in the medium and/or hydantoin reactants and mole ratios can be regulated, as known to one of ordinary skill in the art and from the above description, to produce specific products or product mixes.

In a typical process of a first embodiment of the present invention, a reactor is charged with a quantity of the aqueous stirrable medium or an aqueous stirrable medium is prepared directly in the reactor. The aqueous stirrable medium is then dehydrated as the temperature of the medium is raised so that when the dehydration is complete, i.e., water content is less than one percent by weight, the temperature of the medium is above the melting temperature of the methylolhydantoin(s) or hydantoin(s) that were in the aqueous stirrable medium. This yields a stirrable melt. Typically, this temperature is at least about 80° C. and preferably is at least about 90° C. and ranges to about 110° C., but this temperature will vary depending upon the composition of the stirrable medium. Dehydration typically is accomplished by the application of reduced pressure, i.e. a vacuum or a partial vacuum ranging from about 10 to about 200 mm Hg.

The stirrable melt is then utilized as a "heel" or a medium to which the hydantoin reactant, the substantially anhydrous formaldehyde source, or combination thereof, and optionally, a catalyst are added. The mole ratio of "heel" to hydantoin reactant typically ranges from about 1 to about 0.1. The amounts of any component can be adapted to yield the most efficient utilization of reactor capacity, as is known in the art.

Reactants can be added simultaneously or sequentially, in whole or in part.

The reactant components initially are reacted in the molten state, preferably at a temperature of at least about 80° C. ranging up to about 110° C. The reaction of dehydrated solute formaldehyde or substantially anhydrous formaldehyde, such as para-formaldehyde, with hydantoin yields reaction water from the depolymerization of the para-formaldehyde. Any reaction water is removed from the molten system by any means known to those skilled in the art and preferably by a vacuum means. This yields anhydrous molten methylolhydantoin which is subsequently solidified, typically in a crystalline form.

In an alternative embodiment, the water is removed from a combination of the aqueous stirrable medium and reactants while heating to the melt temperature.

The methods of the present invention may be practiced as batch processes or as semi-continuous processes. In a semicontinuous process, a portion of the molten methylolhydantoin is reserved in the reaction vessel or is transferred to another reaction vessel as a heel for subsequent use, while the remaining portion is solidified, as above, to a solid anhydrous methylolhydantoin product.

Liquid reactor, mixing, and solidification equipment commonly used in the art may be utilized in the present method. All dehydrating, heating, mixing, and addition steps are conducted in conventional manners known to those of ordinary skill in the art.

DESCRIPTION OF THE PREFERRED EMBODIMENTS

The following examples illustrate the invention without limitation. All parts and percentages are given by weight unless otherwise indicated.

The following analytical methods were used. Free formaldehyde was determined by reaction with hydroxylamine hydrochloride. Each mole of formaldehyde liberates one mole of hydrogen chloride. The latter is determined potentiometrically by titration with alkali.

Gas chromatography was used to determine composition (percentage of DMH, MDMH, and DMDMH) in the solutions.

Total formaldehyde was measured by one of two techniques. The first is the Hantzsch method where combined formaldehyde is liberated from the dimethylhydantoin ring by reaction with ammonium acetate and acetylacetone. Combined and free formaldehyde react with the latter two reagents to from 3,5-diacetyl-1,4-dihydrolutidine. The absorbance of the lutidine derivative is measured at 413 nanometers, and the formaldehyde is quantified by comparing to a calibration curve. The second means for measuring total formaldehyde is by alkaline oxidation. Formaldehyde is oxidized with hydrogen peroxide in a solution containing excess potassium hydroxide to form potassium formate. Excess potassium hydroxide is titrated potentiometrically with mineral acid.

Water was measured by the Karl Fischer technique.

THE AQUEOUS MEDIUM/MOLTEN SYSTEM METHOD

Example 1

A 500 ml four-necked round bottom flask, equipped with a magnetic stirrer, a stir bar, a thermometer, a heating mantle, a temperature regulator, a condenser, and a glass stopper, was charged with 243.2 grams (3 moles) of formalin (37% formaldehyde aqueous solution). The pH of the formalin was adjusted to 8.1 with 0.05 gram of 50% sodium hydroxide. 192.2 grams (1.5 moles) of DMH were added at room temperature, and the mixture was stirred as the temperature rose to 40° C. The reaction was allowed to proceed for one hour to yield an aqueous slurry of methylolhydantoin containing 34.4% water, 1.3% free formaldehyde, and 21.5% total formaldehyde.

Another 500 ml four-necked round bottom flask was equipped with an overhead stirrer, a thermometer, a distillation head, and a glass stopper. The distillation head was equipped with a thermometer, a condenser, a graduated cylinder for collecting distillate, and a vacuum connection. Temperature was controlled with an oil bath and a regulator. The flask was charged with a stirrable medium of 183.9 grams of the aqueous slurry of methylolhydantoins and heated. When the temperature reached 40° C., a vacuum (to 56 mm Hg) was applied. The temperature was raised slowly to 95° C. Water began distilling at 60° C. When the temperature reached 95° C., the mixture was held at 56 mm Hg for 30 minutes to yield a stirrable melt. 69.6 grams of water were collected in a cold trap.

The flask was then vented, and 0.38 grams (0.1% by weight of planned solids addition) of sodium bicarbonate catalyst was added. Alternating slugs of 256.3 grams (2 moles) of DMH and 125.4 grams (4 moles) of 95% para-formaldehyde were added to the stirrable melt while the heat was maintained above 80° C. to yield a molten system.

After the addition was completed, the temperature of the molten system was raised to 95° C. and held there for one hour. A vacuum (56 mm Hg) was applied for 45 minutes of this period to yield anhydrous molten methylolhydantoin.

The reaction was then vented, and the molten anhydrous methylolhydantoin was poured onto aluminum foil and allowed to cool to a white crystalline solid.

The solid product was analyzed. Results are illustrated in Table 1.

TABLE 1

| | |
|---|---|
| Total formaldehyde | 30.8% |
| Free formaldehyde | <0.01 |
| Water | 0.58 |
| DMH | 0.3 |
| MDMH | 2.6 |
| DMDMH | 96.8 |
| Polymethylolhydantoin | 0.3 |

Example 2

A 500 ml four-necked flask was equipped with an overhead stirrer, a thermometer, a distillation head, and a glass stopper. The distillation head was equipped with a thermometer, a condenser, a graduated cylinder for collecting distillate, and a vacuum connection. The flask was charged with an aqueous stirrable medium of 111.3 grams of nominal 55% DMDMH/MDMH aqueous solution and 0.35 gram of sodium bicarbonate catalyst. The medium was stirred. A premix of 268.7 grams (2.1 moles) of DMH and 125.8 grams (3.98 moles) of 95% para-formaldehyde was then added over 15 minutes as heat was applied so that the temperature reached 39° C. at the end of the addition. A vacuum (62 mm Hg) was then applied and maintained as the temperature was raised to 101° C. over one and one half hours. About 50 g of water were recovered.

This product was solidified to a white crystalline solid. Analysis revealed that the product contained 30.8 percent total formaldehyde, 0.02 percent free formaldehyde, and 0.48% water.

THE CONSOLIDATED SYSTEM METHOD

Example 3

A 500 ml four-necked flask was equipped with an overhead stirrer, a thermometer, a distillation head, and a glass stopper. The distillation head was equipped with a thermometer, a condenser, a graduated cylinder for collecting distillate, and a vacuum connection. The flask was charged with 53.0 grams of water and, then with 176.0 grams of DMH to yield a stirrable medium of a thick, but stirrable, slurry. Another 24.9 grams of water were added, and the temperature was raised to 41° C. Another 80.5 grams (2 moles total) of DMH were added. The mixture was heated to 53° C. and held for 45 minutes.

126.4 grams (4 moles) of 95% para-formaldehyde were added over a 15 minute period. Heat was applied again. When the temperature reached 72° C., a light vacuum (48 mm Hg) was applied to remove water. Over the next two hours, the temperature was raised to 98° C., and the vacuum was gradually increased to 56 mm Hg.

The product was solidified. Analysis revealed that the product contained 30 percent total formaldehyde, <0.01 percent free formaldehyde, and 0.8 percent water.

THE SEMICONTINUOUS AQUEOUS MEDIUM/MOLTEN SYSTEM METHOD

Example 4

The procedure of Example 1 is followed. However, after discharge of the product onto the aluminum foil, 120 grams of molten product remains in the flask as a stirrable medium. Over about 25 minutes, 0.38 gram of sodium bicarbonate, and then alternating slugs of 256.3 grams (2 moles) of DMH and 126.4 grams (4 moles) of 95% para-formaldehyde are added. The temperature is maintained at 95° C. to 97° C., and a vacuum is gradually applied to 62 mm Hg as water is removed over the next one hour and 45 minutes.

The product is solidified and analysis reveals that the product contains 30.8 percent total formaldehyde, 0.01 percent free formaldehyde, and 0.41 percent water.

THE AQUEOUS MEDIUM/MOLTEN SYSTEM METHOD

Example 5

A 500 ml four necked flask was equipped with an overhead stirrer, a thermometer, a distillation head, and a glass stopper. The distillation head was equipped with a thermometer, a condenser, a graduated cylinder for collecting distillate, and a vacuum connection. The flask was charged with a stirrable medium of 111.3 grams of a nominal 55% DMDMH/MDMH aqueous solution having 18.1% total formaldehyde, 0.83% free formaldehyde, and 45% water. The medium was dehydrated under vacuum (56 mm Hg) as the temperature was raised to 95° C., to yield a stirrable melt. The melt was analyzed and found to contain 31.1% total formaldehyde, 0.05% free formaldehyde, and 0.82% water.

The melt was stirred, and then, a premix of 256.3 grams (2 moles) of DMH and 126.4 grams (4 moles) of 95% para-formaldehyde was added over 15 minutes as heat was applied, so that the temperature reached 39° C. at the end of the addition. A vacuum (62 mm Hg) was then applied and maintained. The temperature was raised to 101° C. over one and one half hours. About 50 grams of water were recovered.

The product was solidified to a white crystalline solid. Analysis revealed that the product contained 31.7% total formaldehyde, <0.01% free formaldehyde, and 0.44% water.

All patents and test methods mentioned above are hereby incorporated by reference.

Many variations of the present invention will suggest themselves to those skilled in the art in light of the above detailed description. Such obvious variations are within the full intended scope of the appended claims.

We claim:

1. A method for producing solid anhydrous methylolhydantoin comprising:
    (a) dehydrating and heating an aqueous stirrable medium to yield a substantially anhydrous stirrable melt, said aqueous stirrable medium comprising:
        (A) a solute selected from the group consisting of
            (i) dimethyloldimethylhydantoin,
            (ii) a hydantoin reactant,
            (iii) a formaldehyde source reactant, or
            (iv) a combination of any of the foregoing; and
        (B) optionally a catalyst;
    (b) providing a molten system by adding to said stirrable melt, a reactant mixture comprising:
        (A) (i) the same or a different hydantoin reactant,
            (ii) a substantially anhydrous formaldehyde source reactant which may be the same as or different than said formaldehyde source reactant, or
            (iii) a combination thereof; and
        (B) optionally, the same or a different catalyst;
    wherein said molten system includes (i) at least one hydantoin reactant and (ii) at least one dehydrated formaldehyde source reactant or substantially anhydrous formaldehyde source reactant;
    (c) reacting (i) said at least one hydantoin reactant and (ii) said at least one dehydrated formaldehyde source reactant or substantially anhydrous formaldehyde source reactant in said molten system, while removing reaction water, to yield anhydrous molten methylolhydantoin; and
    (d) solidifying said molten methylolhydantoin.

2. A method as defined in claim 1, wherein said solid anhydrous methylolhydantoin comprises monomethyloldimethylhydantoin, dimethyloldimethylhydantoin, or a combination of the foregoing.

3. A method as defined in claim 1, wherein said dehydrating of step (a) is conducted at a reduced pressure ranging from 10 to 200 mm Hg.

4. A method as defined in claim 1, wherein said molten system has a temperature ranging from about 80° C. to about 110° C.

5. A method as defined in claim 1, wherein said dehydrating of step (a) is conducted at a reduced pressure ranging from 10 to 200 mm Hg and said heating of step (a) is to a temperature ranging from about 80° C. to about 110° C.

6. A method as defined in claim 1, wherein said reaction water in step (c) is removed by a vacuum means.

7. A method as defined in claim 1, wherein said method is a batch process.

8. A method as defined in claim 1, wherein said method is a semi-continuous process.

9. A method as defined in claim 8, wherein step (d) comprises:

(1) reserving a first portion of said molten methylolhydantoin as a stirrable melt and repeating steps (b)–(d); and (2) solidifying a second portion of said molten methylolhydantoin.

10. A method as defined in claim 1, wherein said hydantoin reactant in said molten system is dimethylhydantoin and said dehydrated formaldehyde reactant or substantially anhydrous formaldehyde source reactant in said molten system is paraformaldehyde.

11. A method as defined in claim 10, wherein said dimethylhydantoin and said para-formaldehyde are added in a mole ratio ranging from about 1:1 to about 1:2.

12. A method as defined in claim 1, wherein the mole ratio of said stirrable melt to said hydantoin reactant in said molten system ranges from about 1:1 to about 1:10.

13. A method for producing solid anhydrous methylolhydantoin comprising:

(a) reacting, to yield a molten methylolhydantoin, a reactant mixture comprising (i) a hydantoin reactant, (ii) a substantially anhydrous formaldehyde source reactant, or (iii) a combination thereof: and (iv) optionally, a catalyst; in an aqueous stirrable medium, said aqueous stirrable medium comprising:

(A) a solute selected from the group consisting of
  (i) dimethyloldimethylhydantoin,
  (ii) the same or a different hydantoin reactant,
  (iii) a formaldehyde source reactant which may be the same as or different than said substantially anhydrous formaldehyde source reactant, or
  (iv) a combination of any of the foregoing; and
(B) optionally, the same or a different catalyst;

wherein (i) at least one hydantoin reactant and (ii) at least one formaldehyde source reactant or substantially anhydrous formaldehyde source reactant is present;

while heating to at least the melting temperature of said anhydrous methylolhydantoin; and while removing substantially all water; and (b) solidifying said molten methylolhydantoin.

14. A method as defined in claim 13, wherein said solid anhydrous methylolhydantoin comprises monomethyloldimethylhydantoin, dimethyloldimethylhydantoin, or a combination of the foregoing.

15. A method as defined in claim 13, wherein said removing of water is conducted under a reduced pressure ranging from about 10 to about 200 mm Hg.

16. A method as defined in claim 13, wherein said heating is to a temperature ranging from about 80° C. to about 110° C.

17. A method as defined in claim 13, wherein said removing of water is conducted under a reduced pressure ranging from about 10 to about 200 mm Hg and said heating is to a temperature ranging from about 80° C. to about 110° C.

18. A method as defined in claim 13, wherein said method is a batch process.

19. A method as defined in claim 13, wherein said method is a semi-continuous process.

20. A method as defined in claim 19, wherein step (b) comprises:

(1)(i) reserving a first portion of said molten methylolhydantoin as a stirrable medium and repeating steps (a) and (b); and, (2) solidifying a second portion of said molten methylolhydantoin.

21. A method as defined in claim 13, wherein said hydantoin reactant is dimethylhydantoin and said formaldehyde source reactant or substantially anhydrous formaldehyde source reactant is para-formaldehyde.

22. A method as defined in claim 21, wherein said dimethylhydantoin and said para-formaldehyde are reacted in a mole ratio ranging from about 1:1 to about 1:2.

23. A method as defined in claim 13, wherein the mole ratio of said stirrable medium to said hydantoin reactant ranges from about 1:1 to about 1:10.

* * * * *